United States Patent [19]

Ward

[11] 4,443,461

[45] Apr. 17, 1984

[54] N-[2-[[1-[1H-INDOLYLALKYL- OR OXOALKYL]-4-PIPERIDINYL]-AMINO]-2-OXOETHYL]ARYLCARBOXAMIDE DERIVATIVES

[75] Inventor: Terence J. Ward, Slough, England

[73] Assignee: John Wyeth & Brother Limited, Maidenhead, England

[21] Appl. No.: 416,773

[22] Filed: Sep. 10, 1982

[30] Foreign Application Priority Data

Sep. 10, 1981 [GB] United Kingdom ............... 8127408

[51] Int. Cl.$^3$ ................. A61K 31/445; C07D 409/14; C07D 405/14; C07D 403/06
[52] U.S. Cl. ................... 424/267; 546/194; 546/201
[58] Field of Search ............... 546/201, 194; 424/267

[56] References Cited

U.S. PATENT DOCUMENTS 4,177,279 12/1979 Archibald et al. ............... 546/201

FOREIGN PATENT DOCUMENTS 1498884 1/1978 United Kingdom .

Primary Examiner—Norma S. Milestone
Attorney, Agent, or Firm—George Tranowski

[57] ABSTRACT

The invention concerns compounds of formula

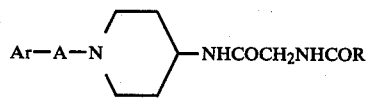

or pharmaceutically acceptable salts thereof, wherein Ar represents an optionally substituted indolyl group; A represents a straight or branched chain alkylene or oxoalkylene group, each having 2-4 carbon atoms and R represents an optionally substituted aryl (including heteroaryl) group, which possess anti-hypertensive and psychotropic activity, and are useful in the treatment of high blood pressure or as anti-depressants.

7 Claims, No Drawings

N-[2-[[1-[1H-INDOLYLALKYL- OR OXOALKYL]-4-PIPERIDINYL]-AMINO]-2-OXOETHYL]ARYLCARBOXAMIDE DERIVATIVES

This invention relates to piperidine derivatives, to processes for preparing them and to pharmaceutical compositions containing them. This invention also relates to pyridinium and tetrahydro pyridinium compounds which are useful as intermediates in the preparation of the piperidine derivatives.

More particularly this invention provides 4-acylaminopiperidyl derivatives which exhibit pharmaceutical activity in warm blooded animals, especially anti-hypertensive activity in standard test procedures and also psychotropic activity as evidenced by their ability to inhibit parachloramphetamine induced hyperactivity. The piperidine compounds are indicated in the treatment of high blood pressure or as antidepressants.

Accordingly this invention provides piperidine derivatives of formula

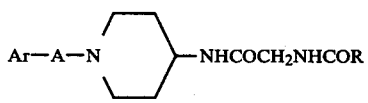

and pharmaceutically acceptable salts thereof, wherein Ar represents an optionally substituted indolyl group; A represents a straight or branched chain alkylene or oxoalkylene group each having 2 to 4 carbon atoms; and R represents an aryl (including heteroaryl) group which may be substituted.

Examples of groups for Ar are indol-3-yl which may be substituted by one or more groups selected from halogen, e.g. fluorine, chlorine or bromine (such as 5-chloro); alkyl having 1 to 6 carbon atoms, e.g. methyl, ethyl and propyl (such as 5-methyl); alkoxy having 1 to 6 carbon atoms, nitro and hydroxy.

Examples of R are phenyl and phenyl substituted by the same groups as mentioned for the radical Ar. Heteroaryl R radicals include radicals where the heteroatom is nitrogen, such as pyridyl, e.g. pyrid-4-yl; sulphur, e.g. thien-2-yl; or oxygen, e.g. furan-2-yl. Heteroaryl R radicals may carry substituents as mentioned for the radical Ar.

Examples of A are —(CH$_2$)$_n$ - where n is 2 or —CO(CH$_2$)$_n$ - where n is 1 to 3, e.g. oxobutylene.

Pharmaceutically acceptable salts of the compounds of formula I include acid addition salts formed with inorganic or organic acids such as the sulphate, hydrochloride, hydrobromide, hydroiodide, nitrate, phosphate, sulphonate (such as the methanesulphonate or p-toluenesulphonate), acetate, maleate, fumarate, tartrate and formate. Quaternary ammonium salts are also included such as those formed with alkyl or aralkyl halides e.g. benzyl chloride, methyl iodide.

This invention also provides processes for preparing compounds of formula (I). In general the compounds of formula (I) can be made prepared by building up the molecule from appropriate starting materials in known manner.

One such process for preparing compounds of formula (I) as defined above comprises acylating a compound of formula:

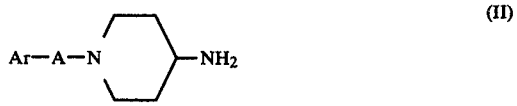

wherein Ar and A are as hereinbefore defined, or a reactive derivative thereof, with an acid of formula:

$$HOOCCH_2NHCOR \qquad (IV)$$

wherein R is as hereinbefore defined, or a reactive derivative thereof. Coupling agents such as dicyclohexylcarbodiimide may be used to effect acylation. As examples of the reactive derivatives of the acid of formula (IV) useful in the above mentioned reaction mention is made of the acid halides, e.g. chloride, the azide and also 2-aryloxazol-5-ones of formula (IVa)

where R is as defined above.

Examples of the compound of formula (II) where the amino function is activated include the phosphazo derivative which may be coupled directly to the acid of formula (IV).

Compounds of formula (II) may be prepared according to processes described in UK Patent Specification Nos. 1218570 and 1345872.

A further process for preparing compounds of formula (I) as defined above comprises reacting a compound of general formula:

$$Ar—A—Y \qquad (V)$$

wherein Ar and A are as defined above and Y represents a leaving group, e.g. a halogen atom or an equivalent replaceable radical, e.g. a sulphonyloxy radical such as tosyloxy, with a compound of formula

wherein R is as hereinbefore defined. Further examples of Y when Ar is indol-3-yl and A is —CH$_2$— are disubstituted amino radicals such as dimethylamino or trisubstituted ammonium radicals such as trimethylammonium (+NMe$_3$).

Yet a further process for preparing a compound of formula (I) comprises aroylating a compound of formula

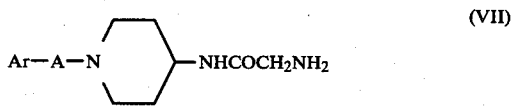

with an aroylating agent containing the group —COR wherein R is as hereinbefore defined e.g. using aroyl halides, aroyl anhydrides. Compounds of formula (VII) may be prepared by removing the α-amino protecting group from a corresponding compound of formula

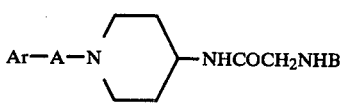

(VIII)

where Ar and n are as hereinbefore defined and B is an α-amino protecting group, e.g. benzyloxycarbonyl, t-butyloxycarbonyl. Methods for removing protecting groups and the protecting groups themselves are described in the standard textbooks on peptide chemistry, see for example e.g. E. Schroder and K. Lubke, "The Peptides" Volume I, Academic Press, New York and London, 1965. Compounds of formula (VIII) may be prepared by coupling a compound of formula (II) as hereinbefore defined with a compound of formula HOOCCH₂NHB where B is as hereinbefore defined.

Compounds of formula (I) may also be prepared by treating a corresponding compound of formula (IX)

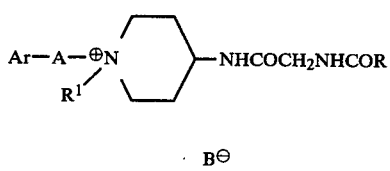

(IX)

to remove $R_1$, wherein Ar and R are as hereinbefore defined, $B^\ominus$ is an anion as hereinbefore defined and $R^1$ is an organic quaternizing group which can be removed under mild conditions, e.g. by hydrogenolysis, that do not affect the rest of the molecule. For example, when $R^1$ is an arylmethyl radical, such as benzyl, hydrogenolysis is under standard conditions, e.g. using an appropriate catalyst such as a palladium on carbon, platinum or nickel catalyst, gives compounds of formula (I). Methods for effecting this reaction are given in our U.K. Patent Specification No. 1,399,608. Suitable solvents include alkanols such as methanol.

Starting materials of formula (IX) may be prepared by reacting a compound of formula (V) as defined above with a compound of formula

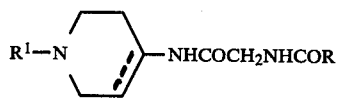

(X)

wherein R and $R^1$ are as defined above, with heating.

Compounds of formula I may also be prepared by reducing a corresponding compound of formula (XI) or (XII):

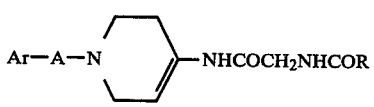

(XI)

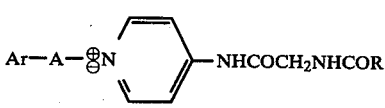

(XII)

in which formulae Ar, A and R are as hereinbefore defined and B⁻ represents an anion, e.g. a halide ion. For example catalytic hydrogenation e.g. in the presence of Raney nickel or platinum catalyst gives piperidine compounds of formula (I). The reduction may also be effected by a process described and claimed in our U.K. Patent Specification No. 1542137. Such a reduction process employs an alkali metal borohydride in a secondary alkanol having 3-5 carbon atoms, e.g. isopropanol. Alternatively reduction of compounds of formula (XII) using an alkali metal borohydride in methanol gives compounds of formula (XI).

Compounds of formula (XI) and (XII) are also within the scope of this invention. They may be prepared by reacting compounds of formula (XIII) and (XIV)

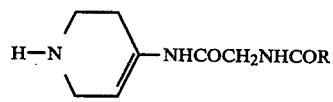

(XIII)

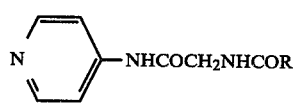

(XIV)

with a compound of formula (V) as hereinbefore defined. Compounds of formula (XIII) may be prepared by reducing a compound of formula (XIV) e.g. using platinum oxide and hydrogen.

Yet a further process for preparing a compound of formula (I) comprises reacting a compound of formula

wherein Ar and A are as hereinbefore defined with a compound of formula VI, in the presence of a catalyst, e.g. a nickel catalyst such as Raney nickel.

Once a compound of formula (I) having a reactive substituent group has been prepared then that compound may be converted in known manner to other compounds of formula (I). For example when Ar is a group having a lower alkoxy or aryl lower alkoxy substituent on an aromatic ring dealkylation produces a corresponding compound of formula (I) wherein Ar carried a hydroxy substituent. When Ar is a group having nitro on an aromatic ring then reduction (e.g. catalytic hydrogenation) can convert the nitro group to an amino group. Such amino groups may be acylated.

The aforementioned processes may also include the step of conversion of an acid addition salt into the base form or vice versa. Quaternisation of the tertiary nitrogen of the piperidine ring may be included as an optional after step, e.g. using alkyl or aryl lower alkyl halides, e.g. methyl iodide, benzyl chloride.

Starting materials used in the above mentioned processes are known compounds or may be prepared by analogous processes for known compounds.

If necessary, in any of the reactions herein described, reactive substituent groups may be blocked during a reaction and released at a later stage. For example an amino substituent may be protected by a benzyloxy-carbonyl group which is removable using H₂/Pd at the end of a reaction. Dehydropiperidine compounds of formula (XI) are also useful as intermediates for preparing the piperidines of formula (I), being converted by reduction.

This invention also includes pharmaceutical compositions containing as active ingredient an active compound of formula (I) as above defined. The active compound may be finely comminuted if desired. In addition to the active ingredient, the compositions also contain a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain 5 to 99, preferably 10–80% of the active ingredient.

Suitable solid carriers are magnesium carbonate, magnesium stearate, talc, sugar, lactose, pectin, dextrine, starch, gelatin, tragacanth, methyl cellulose, sodium carboxylmethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or supended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxylmethyl cellulose solution, or in a suitable oil, for instance arachis oil. Liquid pharmaceutical compositions which are sterile solutions or suspensions can be utilised by intramuscular, intraperitoneal or subcutaneous injection. In many instances, a compound is orally active and can be administered orally either in liquid or solid composition form.

Preferably the pharmaceutical composition is in unit dosage form. In such form, the composition is subdivided in unit doses containing appropriate quantities of the active ingredients; the unit dosage form can be a packaged composition, the package containing specific quantities of composition, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg or less to 500 or more, according to the particular need and the activity of the active ingredient. The invention also includes the compounds in the absence of carrier where the compounds are in unit dosage form.

A further aspect of this invention provides chemical intermediates for the compounds of formula (I) which intermediates have the formula (XI) and (XII) as hereinbefore defined.

The following Examples illustrate the invention

EXAMPLE 1

N-[2-[[1-[2-(1H-indol-3-yl)ethyl]-4-piperidinyl]amino]-2-oxoethyl]benzamide

4-Amino-1-(2-[indol-3-yl]ethyl)piperidine (1.21 g, 5 mmol) and 2-phenyloxazol-5-one (0.8 g, 5 mmol; prepared according to the method of Stewart and Wooley, J.A.C.S. 78 5336 1956) were refluxed in methyl cyanide (30 cm³). After 1½ hours more 2-phenyloxazol-5-one (0.1 g, 0.62 mmol) in methyl cyanide (10 cm³) was added. A further portion of 2-phenyl-oxazol-5-one (0.1 g, 0.62 mmol) was added after 1 hour, and refluxing was continued for 30 minutes. The mixture was filtered hot and the filtrate on cooling gave the crude title compound which was collected and dried (1.55 g). The solid obtained was refluxed in isopropyl alcohol containing ethanolic HCl for three quarters of an hour and to give the hydrochloride salt which was collected after cooling overnight. This was sucked dry on the sinter, triturated with refluxing ethanol for half an hour, collected, then triturated with ethanol containing 5–10% water, filtered hot and dried to give the hydrochloride salt of the title compound (0.77 g) mp 236°–240° C.

Analysis: Found C, 64.50; H, 6.54; N 12.57%; $C_{24}H_{28}N_4O_2$ HCl, ¼ $H_2O$ requires: C,64.71; H, 6.68; N,12.58%

EXAMPLE 2

N-[2-[[1-[2-(1H-indol-3-yl)ethyl]-4-piperidinyl]amino]-2-oxoethyl]-4-pyridinecarboxamide (i) Chloroacetyl chloride (4.0 cm³, 50.18 mmol) was added dropwise to a vigorously stirred mixture of 4-amino-1-(2-[indol-3-yl]ethyl)piperidine (12.10 g, 49.8 mmol), potassium carbonate (7.0 g 50.72 mmol) water (100 cm³) and dichloromethane (300 cm³). After ¾ hour more chloroacetyl chloride (0.5 cm³, 6.27 mmol) and potassium carbonate (0.5 g, 3.62 mmol) were added and stirring continued for a further ¾ hour. The organic phase was separated, washed with water, dried over magnesium sulphate and evaporated to give 2-chloro-N-[1-[2-(1H-indol-3-yl)ethyl]-4-piperidinyl]acetamide (19.29 g crude)

(ii) A solution of the chloro product (3.5 g, 10.95 mmol) in strong ethanolic ammonia (140 cm³) was heated at 100° C. in a bomb for 22 h. This was evaporated to give a glass (3.23 g) which was purified by chromatography on silica (100–200 aktiv) eluting with chloroform 83: methanol 15: triethylamine 2 parts. This gave 0.92 g of 2-amino-N-[1-[2-(1H-indol-3-yl)ethyl]-4-piperidinyl]acetamide.

(iii) The product of step (ii) is acylated with 4-pyridoyl chloride, hydrochloride to give the title compound. m.p. 211°–215° C.

EXAMPLE 3

The following procedure was used to test compounds of formula I for their ability to inhibit p-chloroamphetamine induced hyperactivity.

Three groups of 4 female mice (20–24 g) received the test compounds (50 mg/kg po) and a fourth group the requisite volume of vehicle. Thirty minutes later all the animals are given 20 mg/kg p-chloroamphetamine (pCA) ip. The grouped mice are placed immediately in square plastic cages in activity monitors and their motor activity recorded over the period 10–30 minutes post pCA. This procedure is repeated three more times so that four groups of mice are used per treatment and each activity monitor is used with all treatments in turn. The inhibition of pCA induced hyperactivity is calculated thus:

$$\frac{C-T}{C} \times 100\%$$

where C = mean activity of control groups 10–30 minutes post pCA.

T = mean activity of treated groups 10–30 minutes post pCA.

This test is used as an in vivo screen for detection of 5-hydroxytryptamine uptake inhibitors.

Compounds giving > 50% inhibition are considered of special interest. In such a test the compound of Example 1 showed 51.6% inhibition at 50 mpk.

EXAMPLE 4

The following procedure was used to test compounds of formula I for antihypertensive activity.

Female rats are rendered hypertensive by implanting subcutaneously two wax pellets (30 mg) containing desoxycorticosterone acetate (15 mg) followed immediately by uninephrectomy. The drinking water is replaced by normal saline ad lib for 4 weeks. Blood pressures stabilise at a hypertensive level after 6 weeks. Systolic pressure is measured directly before dosing with a test compound using an E and M pneumatic pulse transducer and a Devices MX2 recorder. Groups of 4 rats are dosed orally with suspensions or solutions of test compound in 0.5% hydroxypropylmethylcellulose 0.9% saline vehicle. Blood pressures are recorded again at various time intervals and the results, expressed as a percentage of the pre-dose values compared with those of a similar group of rats receiving vehicle alone.

In the above test the compound of Example 1 at a dose level of 50 mpk gave a 36.4% decrease in blood pressure after 2 and 6 hours. In the same test heart rate was decreased by 35.9% and 37.7% and 6 hours respectively after dosing.

EXAMPLE 5

Using a procedure analogous to Example 2, the following compounds may be reacted with 2-amino-N-[1-[2-(1H-indol-3-yl)ethyl]-4-piperidinyl]-acetamide
 (a) benzoyl chloride
 (b) 4-chlorobenzoyl chloride
 (c) 4-methoxybenzoyl chloride
 (d) 2-thenoyl chloride
 (e) 3-methylbenzoyl chloride
to give:

(a) N-[2-[[1-[2-(1H-indol-3-yl)ethyl]-4-piperidinyl]amino]-2-oxoethyl]benzamide
 (b) N-[2-[[1-[2-(1H-indol-3-yl)ethyl]-4-piperidinyl]amino]-2-oxoethyl]-4-chlorobenzamide.
 (c) N-[2-[[1-[2-(1H-indol-3-yl)ethyl]-4-piperidinyl]amino]-2-oxoethyl]-4-methoxybenzamide.
 (d) N-[2-[[1-[2-(1H-indol-3-yl)ethyl]-4-piperidinyl]amino]-2-oxoethyl]-2-thiophenecarboxamide.
 (e) N-[2-[[1-[2-(1H-indol-3-yl)ethyl]-4-piperidinyl]amino]-2-oxoethyl]-3-methylbenzamide.

I claim:

1. A compound of formula

or a pharmaceutically acceptable salt thereof wherein Ar represents an indolyl group optionally substituted by one or more groups selected from halogen, alkyl of 1 to 6 carbon atoms, alkoxy of 1 to 6 carbon atoms, nitro or hydroxy; A represents a straight or branched chain alkylene or oxoalkylene group, each having 2 to 4 carbon atoms; and R represents a phenyl, pyrid-4-yl, thien-2-yl or furan-2-yl group optionally substituted by one or more groups selected from halogen, alkyl of 1 to 6 carbon atoms, alkoxy of 1 to 6 carbon atoms, nitro or hydroxy.

2. A compound as claimed in claim 1 wherein Ar is an indol-3-yl group.

3. A compound as claimed in claim 1 wherein R represents a phenyl or pyrid-4-yl group, each of which may be substituted by of least one group selected from lower alkyl, lower alkoxy, halogen.

4. A compound as claimed in claim 1 wherein A is

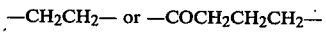

5. A compound as claimed in claim 1 which is N-[2-[[1-[2-(1H-indol-3-yl)ethyl]-4-piperidinyl]amino]-2-oxoethyl]benzamide or a pharmaceutically acceptable salt thereof.

6. A compound as claimed in claim 1 which is N-[2-[[1-[2-(1H-indol-3-yl)ethyl]-4-piperidinyl]amino]-2-oxoethyl]-4-pyridinecarboxamide or a pharmaceutically acceptable salt thereof.

7. A pharmaceutical compound comprising a pharmaceutically effective amount of a compound as claimed in claim 1 or a pharmaceutically acceptable salt thereof and a pharmaceutically acceptable carrier.

* * * * *